(12) United States Patent
Stachon et al.

(10) Patent No.: US 8,537,360 B2
(45) Date of Patent: Sep. 17, 2013

(54) AUTOMATED SOYBEAN PHENOTYPING FOR IRON DEFICIENCY CHLOROSIS

(75) Inventors: Walter Stachon, Northfield, MN (US); Ken Luebbert, Cedar Rapids, IA (US); John Gass, Slater, IA (US)

(73) Assignee: Syngenta Participations AG, Basel (CH)

( * ) Notice: Subject to any disclaimer, the term of this patent is extended or adjusted under 35 U.S.C. 154(b) by 6 days.

(21) Appl. No.: 12/861,583

(22) Filed: Aug. 23, 2010

(65) Prior Publication Data

US 2011/0043805 A1 Feb. 24, 2011

Related U.S. Application Data

(60) Provisional application No. 61/235,908, filed on Aug. 21, 2009, provisional application No. 61/349,018, filed on May 27, 2010, provisional application No. 61/373,471, filed on Aug. 13, 2010.

(51) Int. Cl.
*G01N 21/00* (2006.01)

(52) U.S. Cl.
USPC ........ 356/432; 250/226; 250/338.1; 356/445; 356/407; 356/416; 701/300

(58) Field of Classification Search
USPC ........... 250/221, 226, 338.1, 222.1; 356/432, 356/445, 4.1, 407, 416, 425; 701/213, 50, 701/207, 208, 205, 300
See application file for complete search history.

(56) References Cited

U.S. PATENT DOCUMENTS

| | | | |
|---|---|---|---|
| 5,764,819 A | 6/1998 | Orr et al. | |
| 5,987,384 A * | 11/1999 | Matson | ............................. 702/2 |
| 6,236,739 B1 | 5/2001 | Conrad | |
| 6,505,146 B1 | 1/2003 | Blackmer | |
| 6,596,996 B1 | 7/2003 | Stone et al. | |
| 6,597,991 B1 | 7/2003 | Meron et al. | |
| 7,058,197 B1 | 6/2006 | McGuire et al. | |
| 7,570,783 B2 | 8/2009 | Wei et al. | |
| 7,571,075 B2 | 8/2009 | Glenn et al. | |
| 7,580,549 B2 | 8/2009 | Wei et al. | |
| 7,617,057 B2 | 11/2009 | May et al. | |
| 7,715,013 B2 | 5/2010 | Glaser et al. | |
| 8,027,770 B2 | 9/2011 | Poulsen | |
| 2010/0032495 A1* | 2/2010 | Abts | ............................. 700/284 |

OTHER PUBLICATIONS

Patent Cooperation Treaty, PCT/US2010/046288, International Search Report dated Sep. 29, 2010 and Written Opinion dated Sep. 21, 2010.

(Continued)

*Primary Examiner* — Gregory J Toatley
*Assistant Examiner* — Iyabo S Alli
(74) *Attorney, Agent, or Firm* — R. Kody Jones

(57) ABSTRACT

A system for evaluating the susceptibility of a soybean plant to iron deficiency chlorosis is described. Soybean plants are planted in range and rows multiple micro-plots and a cart is used to pass a radiometric sensor over the micro-plots. The cart may have a sensor housing that is divided into multiple partitions with a radiometric sensor assembly positioned within each partition. Each sensor assembly generates a data signal and a computer receives and stores the data signals. The field cart is positioned above the range. The number of partitions corresponds to the number of rows in the range and each sensor assembly is positioned above a single row.

10 Claims, 12 Drawing Sheets

(56) References Cited

OTHER PUBLICATIONS

Patent Cooperation Treaty, PCT/US2010/046303, International Search Report dated Sep. 30, 2010 and Written Opinion dated Sep. 22, 2010.
Patent Cooperation Treaty, PCT/US2010/046315, International Search Report dated Oct. 1, 2010 and Written Opinion dated Sep. 23, 2010.
Sensible Solutions—News & Information for on the Go Sensing. GreenSeeker Mapping Capabilities. http://www.nue.okstate.edu. GreenSeeker Winter 2007. vol. 1, Issue 1, p. 1-3.
Thompson, NDVI imagery determines harvest strategies. 2008. http://spaa.com.au/files/catalog/springsummer2008.
Ma, et al., Early Prediction of Soybean Yield from Canopy Reflectance Measurements, Agron.J.93:1227-1234 (2001).
Tucker et al., Monitoring corn and Soybean Crop Development with Hand-Held Radiometer Spetral Data, Remote Sensing of Environment, 8:237-248 (1979).
NTech Industries, Inc., GreenSeeker Desktop Mapper literature.
Holland Scientific Drop Circle Mapping System literature.
Yara N Sensor literature.
Konica Minolta SPAD 502 Plus Chlorophyll Meter literature.
Tucker, et al., Temporal Spectral measurements of Corn and Soybean Crops, Photogrammertic Eng. and Remote Sensing 45 5:643-653 (1979).
Montes, et al., Novel throughput phenotyping platforms in plant genetic studies, Trends in Plant Science vol. 12, Issue 10, 433-436, 2007 Montes, et.al.
Ruckelshausen, et al., 10th International Conference on Precision Agriculture, 2010.
Solari, et al, Active Sensor Reflectance Measurement of corn Nitrogen Status and Yield Potential, AgronomyJournal, 100:571-579 (2008).
Moroni, et al, Variation in Normalized Difference Vegetative Indes (NDVI) in canola germplasm, 16th Australian research Assembly, 2009.
Govaerts, et al, The normalized difference vegetation index (NDVI) GreenSeekerTM handheld sensor: Toward the integrated evaluation of crop management, CIMMYT, 2010.
Cianzio, et al, Genotypic Evaluation for lorn Deficiency Chlorosis in Soyeans by Visual Scores adn Chlorophyll Concentration, Crop Sci. 19:644-646 (1979).
Rogovska, et al., Remote sensing of soybean canopy as a tool to map high pH, calcareous soils at field scale, Precision Agric. 10:175-187 (2009).
Hansen, et al, Iron Deficiency of Soybean in the Upper Midwest and Associated Soil Properties, Agron.J.95:1595-1601 (2003).

\* cited by examiner

US 8,537,360 B2

AUTOMATED SOYBEAN PHENOTYPING FOR IRON DEFICIENCY CHLOROSIS

CROSS REFERENCE TO RELATED APPLICATION

This application claims benefit of U.S. Provisional Application Ser. No. 61/235,908 filed Aug. 21, 2009, U.S. Provisional Application Ser. No. 61/349,018 filed May 27, 2010 and U.S. Provisional Application Ser. No. 61/373,471 filed Aug. 13, 2010 which are incorporated herein by reference in their entirety.

BACKGROUND OF THE INVENTION

The present invention relates to a system for automated soybean phenotyping for iron deficiency chlorosis. More specifically, the invention relates to a field cart for use in an automated soybean phenotyping system, and also to methods of selecting plants based on the automated soybean phenotyping system.

Iron Deficiency Chlorosis (IDC) is a condition that can occur in high pH soils (greater than about 7.5), and is associated not only with low iron content of the soil but also with high calcium carbonate, soluble salt, and nitrate levels. Iron is necessary for the formation of chlorophyll, which is the green pigment in plants. When the amount of iron available to plants is inadequate for normal growth whether through insufficient iron levels (rare) or due to the low solubility of iron at high pH, leaves become pale green, yellow or white, particularly between the veins. This loss of green color is called chlorosis. The effect of chlorosis on the plant is reduced growth and yield. Selection of resistant or tolerant varieties is a key to managing IDC. Accordingly, it is important to screen soybean plants for susceptibility to IDC during the evaluation of plants for promotion in breeding programs. A method for IDC screening that is faster and provides more consistent and reliably data will assist in the development of resistant or tolerant varieties that will enhance the production of soybeans.

SUMMARY OF THE INVENTION

The invention consists of a system and a field cart used in soybean plant breeding programs to automate phenotyping of soybean plants to screen for susceptibility (or tolerance) of the plants to IDC.

The system automates the process of screening thousands of experimental soybean plants for IDC. Typically, soybean phenotyping for IDC is a manual process that relies on several experienced technicians to make and record hundreds of evaluations per hour. This manual system uses a numerical rating system from one to nine, where one equals no chlorosis and nine equals plant death. Thousands of plots must be manually evaluated on a daily basis by multiple technicians. The evaluations are subjective because of differing biases and amount of experience of each technician. A technician can typically evaluate between 500 and 1000 plants per hour.

In one embodiment, the invention provides a system for phenotyping growing soybean plants. The invention is used to evaluate the phenotypic status of soybean plants growing in a field that is divided into multiple plots. Apparatus for taking phenotypic data are mounted on a field cart for easy transport in the plots of the field. The field cart includes a body supported on wheels above the plant canopy and a sensor housing secured to the body. The sensor housing is divided into multiple partitions with a downward-looking sensor assembly positioned within each partition. The number of partitions corresponds to the number of rows of soybean plants that are spanned by the cart so that each partition is positioned above a row. As the cart is pushed down the plurality of rows, each sensor assembly collects data from the plants in the corresponding row and generates a data signal that is received and stored in a computer also mounted on the cart. Preferably, the position of each soybean plant in each row of the field or range was recorded by GPS apparatus associated with a planter that planted the row and the field cart also includes GPS apparatus such that the data generated can be correlated with the recorded planting position and hence the identity of the seed planted at the location for use in a breeding program for developing IDC resistant or tolerant varieties of soybeans.

In another embodiment, the invention provides a field cart for phenotyping growing soybean plants. The field cart includes a body supported on a plurality of wheels and a sensor housing secured to the body. The sensor housing includes multiple partitions with a sensor assembly positioned within each partition. Each sensor assembly generates a data signal and a computer receives and stores the data signals.

In another embodiment, the invention provides a method of phenotyping growing soybean plants. The method includes planting a plurality of rowed plots in a field and positioning a wheeled field cart for phenotyping above the growing plants. The field cart includes a body with a sensor housing secured to the body. The sensor housing includes multiple partitions with a sensor assembly positioned within each partition. Each sensor assembly generates a data signal and a computer receives and stores the data signals. The method also includes the steps of positioning each sensor assembly above a single row of a plot in the range, scanning each plant in each row, transmitting a data signal from each sensor assembly to the computer, and storing the data signals in the computer.

Other aspects of the invention will become apparent by consideration of the detailed description and accompanying drawings.

DETAILED DESCRIPTION OF PREFERRED EMBODIMENTS

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The apparatus and methodologies described herein may make advantageous use of the Global Positioning Satellite (GPS) system to determine and record the positions of fields, plots within the fields and plants within the plots and to correlate collected plant condition data. Although the various methods and apparatus will be described with particular reference to GPS satellites, it should be appreciated that the teachings are equally applicable to systems which utilize pseudolites or a combination of satellites and pseudolites. Pseudolites are ground- or near ground-based transmitters which broadcast a pseudorandom (PRN) code (similar to a GPS signal) modulated on an L-band (or other frequency) carrier signal, generally synchronized with GPS time. Each transmitter may be assigned a unique PRN code so as to permit identification by a remote receiver. The term "satellite", as used herein, is intended to include pseudolites or equivalents of pseudolites, and the term GPS signals, as used herein, is intended to include GPS-like signals from pseudolites or equivalents of pseudolites.

It should be further appreciated that the methods and apparatus of the present invention are equally applicable for use with the GLONASS and other satellite-based positioning systems. The GLONASS system differs from the GPS system in that the emissions from different satellites are differentiated from one another by utilizing slightly different carrier frequencies, rather than utilizing different pseudorandom codes. As used herein and in the claims which follow, the term GPS should be read as indicating the United States Global Positioning System as well as the GLONASS system and other satellite- and/or pseudolite-based positioning systems.

Figure 1:
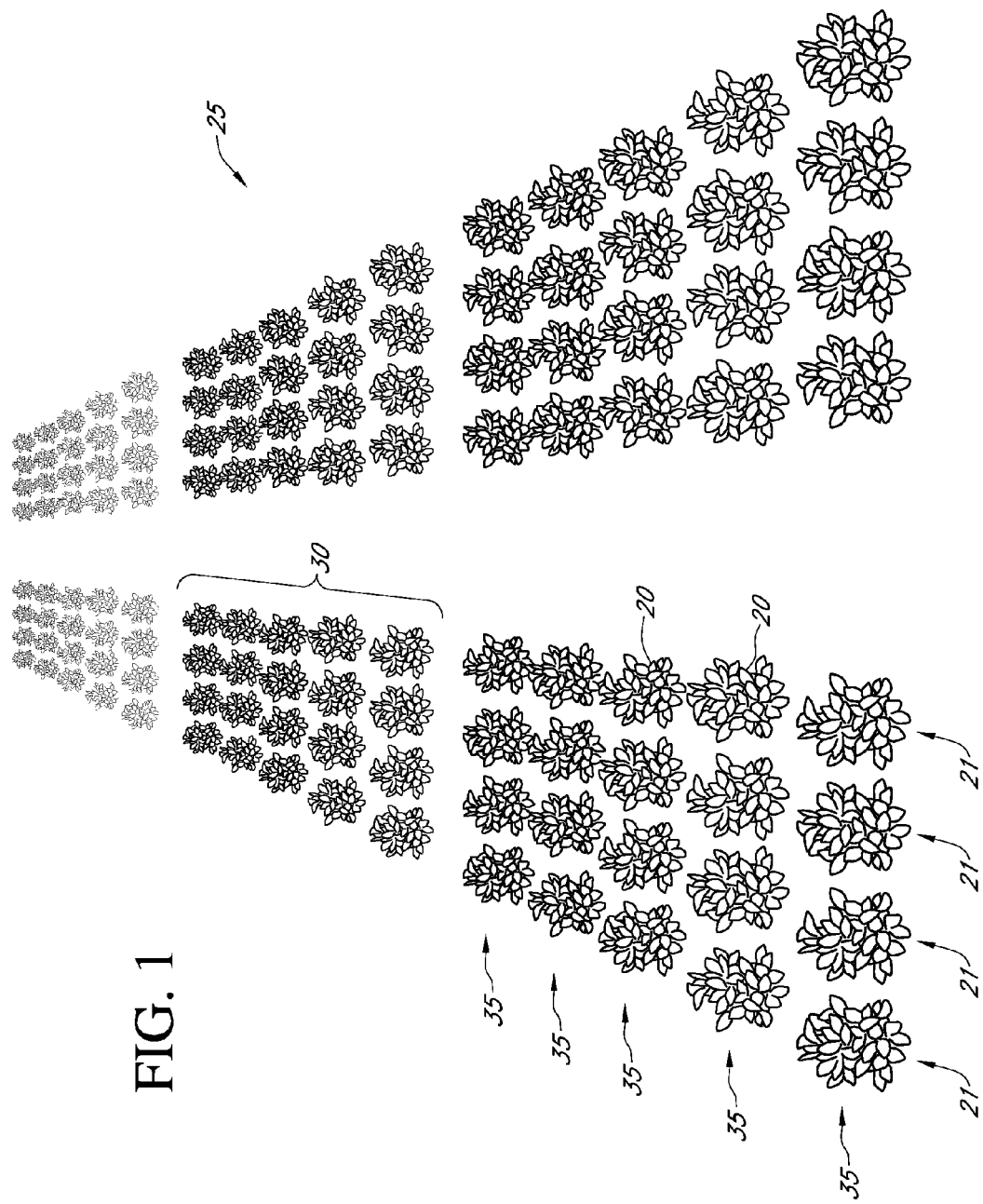
FIG. 1 is a perspective view of a soybean field.

FIG. 1 illustrates an agricultural field 25 which has been planted in accordance with the methods described herein. A planter equipped with a high-precision GPS receiver results in the development of a digital map of the agricultural field 25. The map defined through this operation may become the base map and/or may become a control feature for a machine guidance and/or control system to be discussed in further detail below. The map should be of sufficient resolution so that the precise location of a vehicle within the area defined by the map can be determined to a few inches with reference to the map. Currently available GPS receivers, for example as the ProPak®-V3 produced by NovAtel Inc. (Calgary, Alberta, Canada) are capable of such operations.

For the operation, a tractor or other vehicle is used to tow a planter across the field 25. The planter is fitted with a GPS receiver which receives transmissions from GPS satellites and a reference station. Also on-board the planter is a monitoring apparatus which records the position of seeds as they are planted by the planter. In other words, using precise positioning information provided by the GPS receiver and an input provided by the planter, the monitoring apparatus records the location at which each seed is deposited by the planter in the field 25.

As the tractor and planter proceeds across field 25 to plant various rows of seeds or crops, a digital map is established wherein the location of each seed planted in field 25 is stored. Such a map or other data structure which provides similar information may be produced on-the-fly as planting operations are taking place. Alternatively, the map may make use of a previously developed map (e.g., one or more maps produced from earlier planting operations, etc.). In such a case, the previously stored map may be updated to reflect the position of the newly planted seeds. Indeed, in one embodiment a previously stored map is used to determine the proper location for the planting of the seeds/crops.

In such an embodiment, relevant information stored in a database, for example the location of irrigation systems and/or the previous planting locations of other crops, may be used to determine the location at which the new crops/seeds should be planted. This information is provided to the planter (e.g., in the form of radio telemetry data, stored data, etc.) and is used to control the seeding operation. As the planter (e.g., using a conventional general purpose programmable microprocessor executing suitable software or a dedicated system located thereon) recognizes that a planting point is reached (e.g., as the planter passes over a position in field 10 where it has been determined that a seed should be planted), an onboard control system activates a seed planting mechanism to deposit the seed. The determination as to when to make this planting is made according to a comparison of the planter's present position as provided by the GPS receiver and the seeding information from the database. For example, the planting information may accessible through an index which is determined according to the planter's current position (i.e., a position-dependent data structure). Thus, given the planter's current location, a look-up table or other data structure can be accessed to determine whether a seed should be planted or not.

In cases where the seeding operation is used to establish the digital map, the seeding data need not be recorded locally at the planter. Instead, the data may be transmitted from the planter to some remote recording facility (e.g., a crop research station facility or other central or remote workstation location) at which the data may be recorded on suitable media. The overall goal, at the end of the seeding operation, is to have a digital map which includes the precise position (e.g., to within a few inches) of the location of each seed planted. As indicated, mapping with the GPS technology is one means of obtaining the desired degree of accuracy.

As shown in FIG. 1, soybean phenotyping for IDC is conducted on soybean micro-plots 20 planted in a group of four rows 21. The field 25 is made up of multiple groupings of rows. A micro-plot 20 is a grouping of multiple soybean plants all planted at the same time. For example, a micro-plot 20 is a grouping of the soybean plants resulting from the planting often-soybean seeds. A micro-plot 20 is ten inches long in the direction of the rows 21. Each micro-plot 20 is planted with the same variety of soybean.

Figure 2:
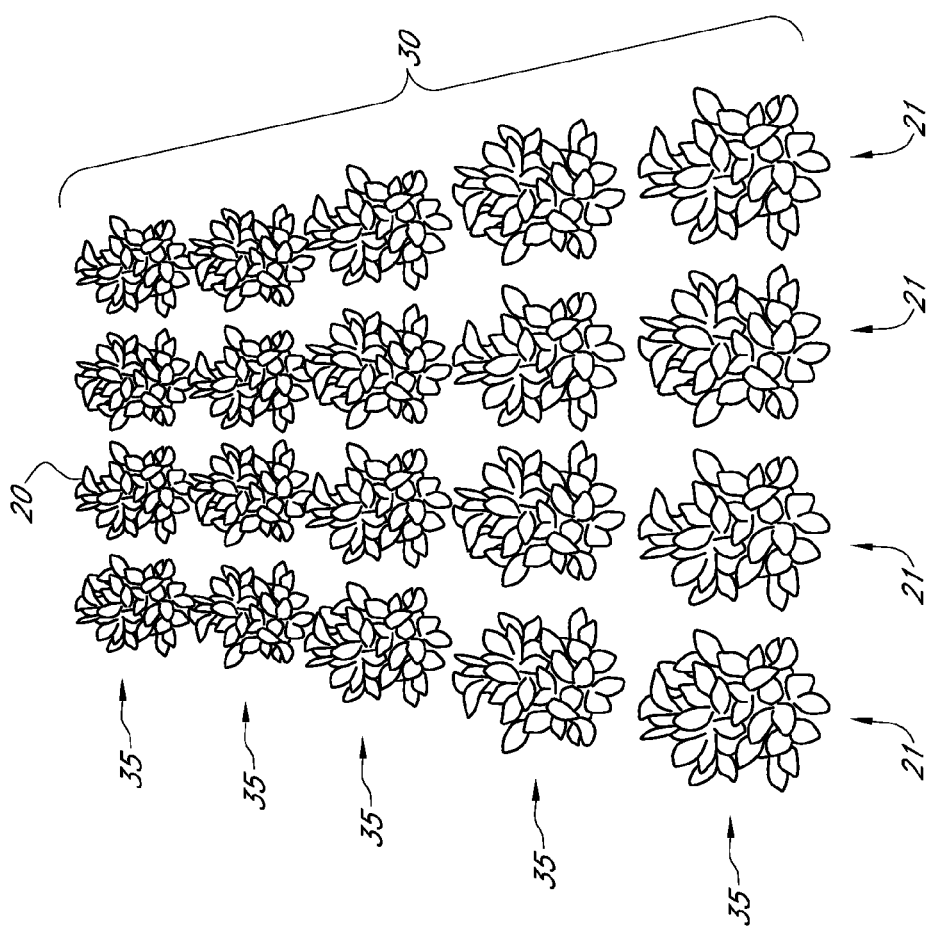
FIG. 2 is a perspective view of a block or plot of soybean plants.
Figure 3:
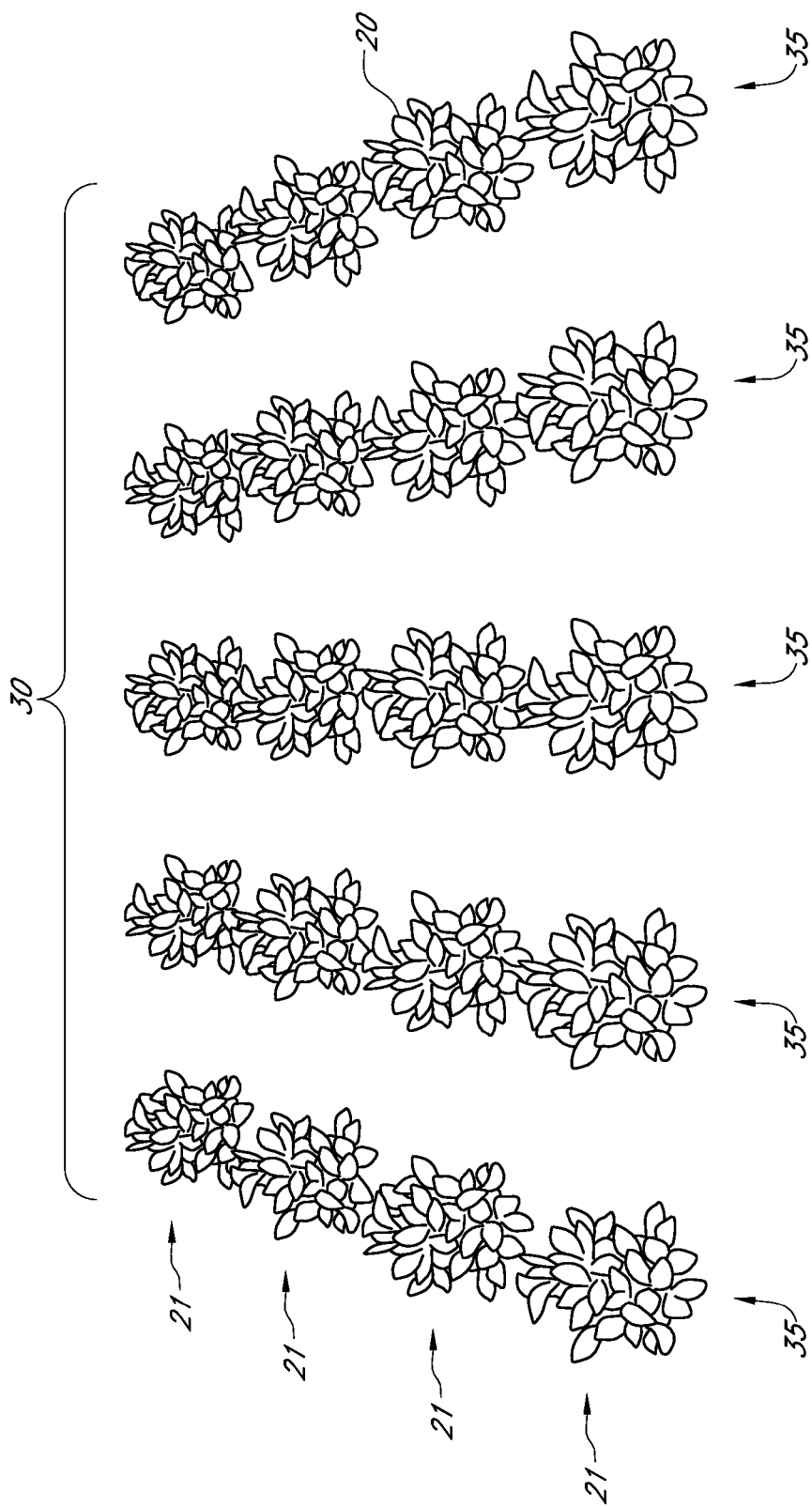
FIG. 3 is another perspective view of a block of soybean plants.

As shown in FIGS. 2 and 3, the micro-plots 20 are arranged in a block 30 including five ranges 35 across four rows 21 for a total of twenty micro-plots 20. Multiple blocks 30 are planted in the field 25. In a preferred embodiment, the ranges 35 are separated by a distance of fifteen inches. Within each range 35, the center of each micro-plot 20 is spaced ten inches from the center of an adjacent micro-plot 20; i.e., each row 21 is positioned 10 inches away from its adjacent row(s) 21. In other embodiments, the block 30 includes a different total number of micro-plots 20, is arranged with a different number of rows 21, is arranged with a different number of ranges 35, and is planted with different spacing between micro-plots 20.

Different varieties of soybeans are planted in the field 25 as part of a breeding program to determine varieties that are resistant, tolerant, or susceptible to IDC. In a preferred embodiment, experiments are conducted in groups of two blocks 30 consisting of a total of forty micro-plots 20. Thirty-six micro-plots 20 are used for testing and four micro-plots 20 are used as indicators. The four indicator micro-plots 20 include varieties of known resistance to IDC. For example, the four indicator micro-plots 20 include one micro-plot 20 susceptible to IDC, one micro-plot 20 tolerant to IDC, and two micro-plots 20 of intermediate resistance. The indicator micro-plots 20 function as a known for data gathering purposes. For example, if all of the indicator micro-plots 20 show no effects of IDC, the data associated with the testing micro-plots 20 is suspect and requires further evaluation to determine why all the indicator micro-plots 20 show no effects of IDC.

Plants absorb and reflect specific wavelengths of light across the spectrum of light. The pattern of reflectance and absorbance changes through the life cycle of the plant. Using plants with predetermined characteristics (for example, plants without IDC or controls), indices of specific wavelengths of reflected energy are created that correlate with the condition of the plant.

The apparatus and methodologies described herein utilize radiometric crop sensor assemblies 40 that measure the reflectance and absorbance of one or more frequencies of light by plant tissues. There are two types of radiometric sensor assemblies 40, active sensor assemblies which use one or more internal light sources to illuminate the plants being evaluated, and passive sensor assemblies which use ambient light only. One suitable index in assessing crop conditions is the normalized difference vegetative index (NDVI). The NDVI was developed during early use of satellites to detect living plants remotely from outer space. The index is defined as NDVI=(NIR−R)/(NIR+R) where NIR is the reflectance in the near infrared range and R is the reflectance in the red range but other visual frequencies can be substituted for red. Preferred sensors for use with the present invention generate an output that is in NDVI units.

Figure 4:
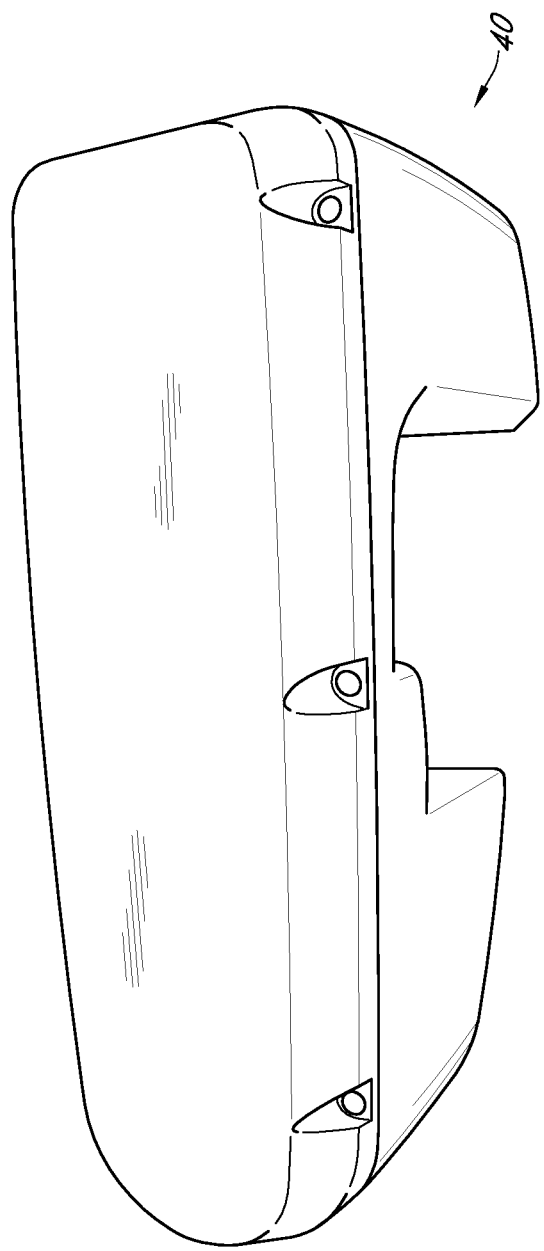
FIG. 4 is a perspective view of a sensor assembly.
Figure 5:
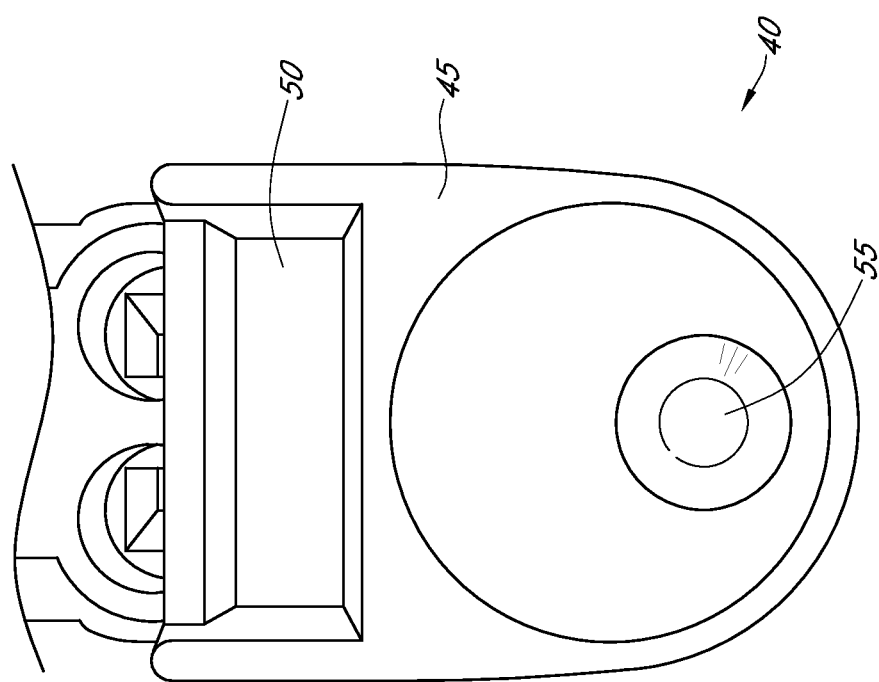
FIG. 5 is a bottom view of the sensor assembly of FIG. 4.

As shown in FIGS. 4 and 5, a preferred sensor assembly 40 is the GreenSeeker® RT100 sold by NTech Industries (Ukiah, Calif.), now a part of Trimble Navigation Limited (Sunnyvale, Calif.). In other embodiments, passive sensor assemblies that utilize ambient light are used.

As shown in FIG. 5, a radiometric sensor assembly 40 includes a casing 45, a light source 50 mounted in the casing 45, and a sensor 55 mounted in the casing 45. In some embodiments, the sensor assembly 40 includes a sensor module including the light source 50 and the sensor 55 and a control box electrically connected to the sensor module. In other embodiments, the sensor assembly 40 includes multiple sensors 55 and multiple light sources 50. As explained above, the sensor 55 is configured to measure the reflectance and absorbance of one or more frequencies of light by plant tissues and generate an output in NDVI units.

Figure 6:
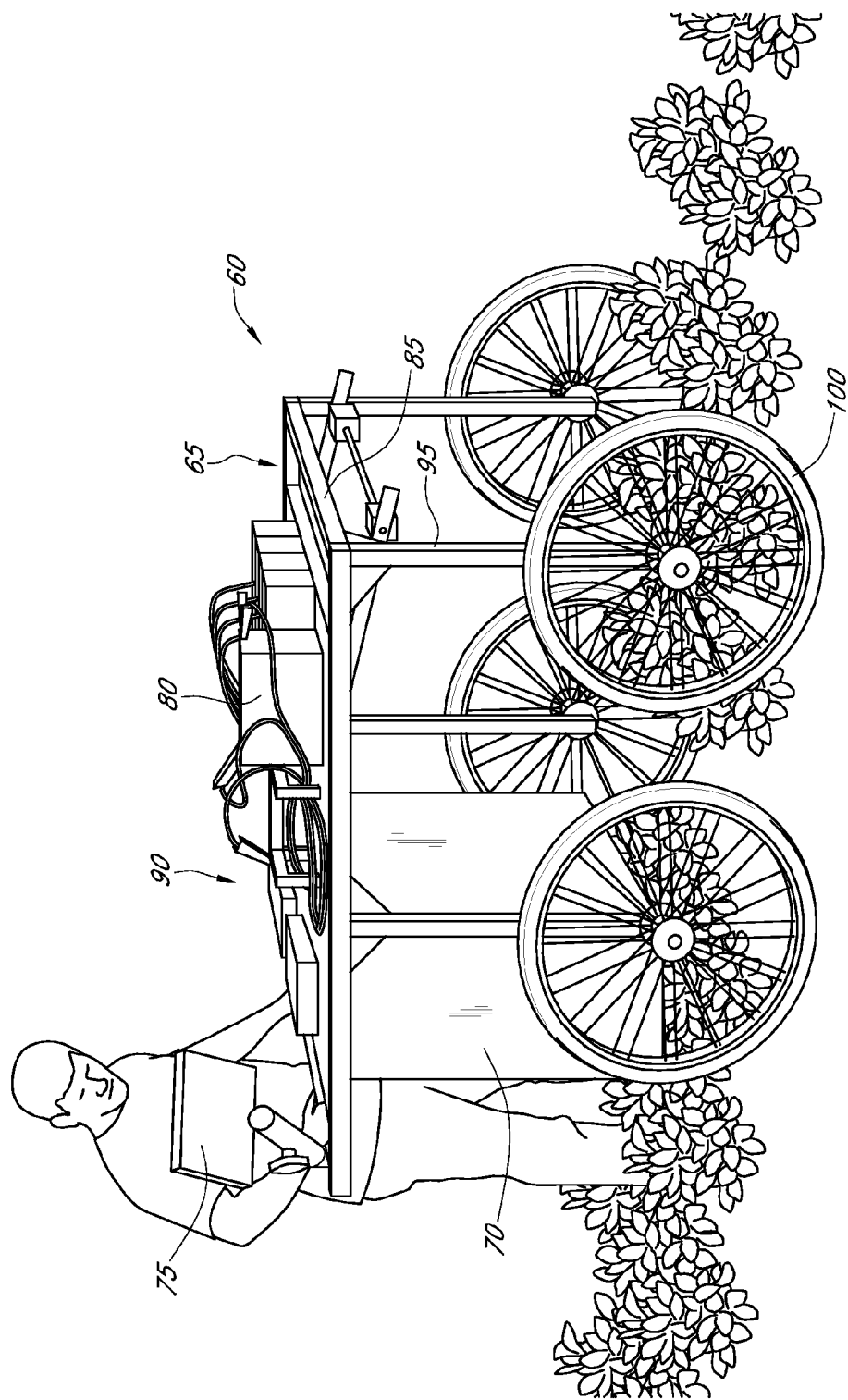
FIG. 6 is a perspective view of a field cart.
Figure 11:
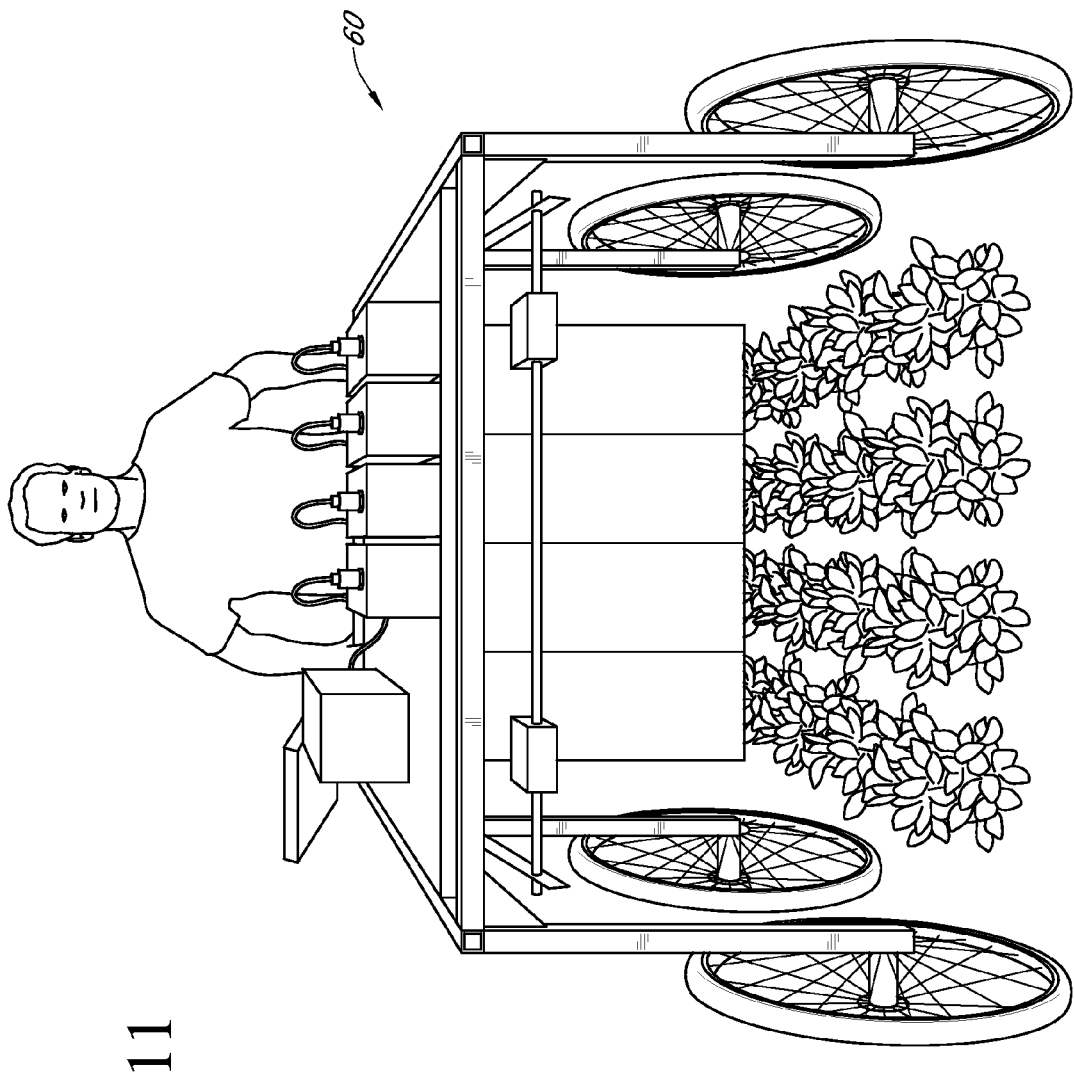
FIG. 11 is a front perspective view of the field cart of FIG. 6.
Figure 12:
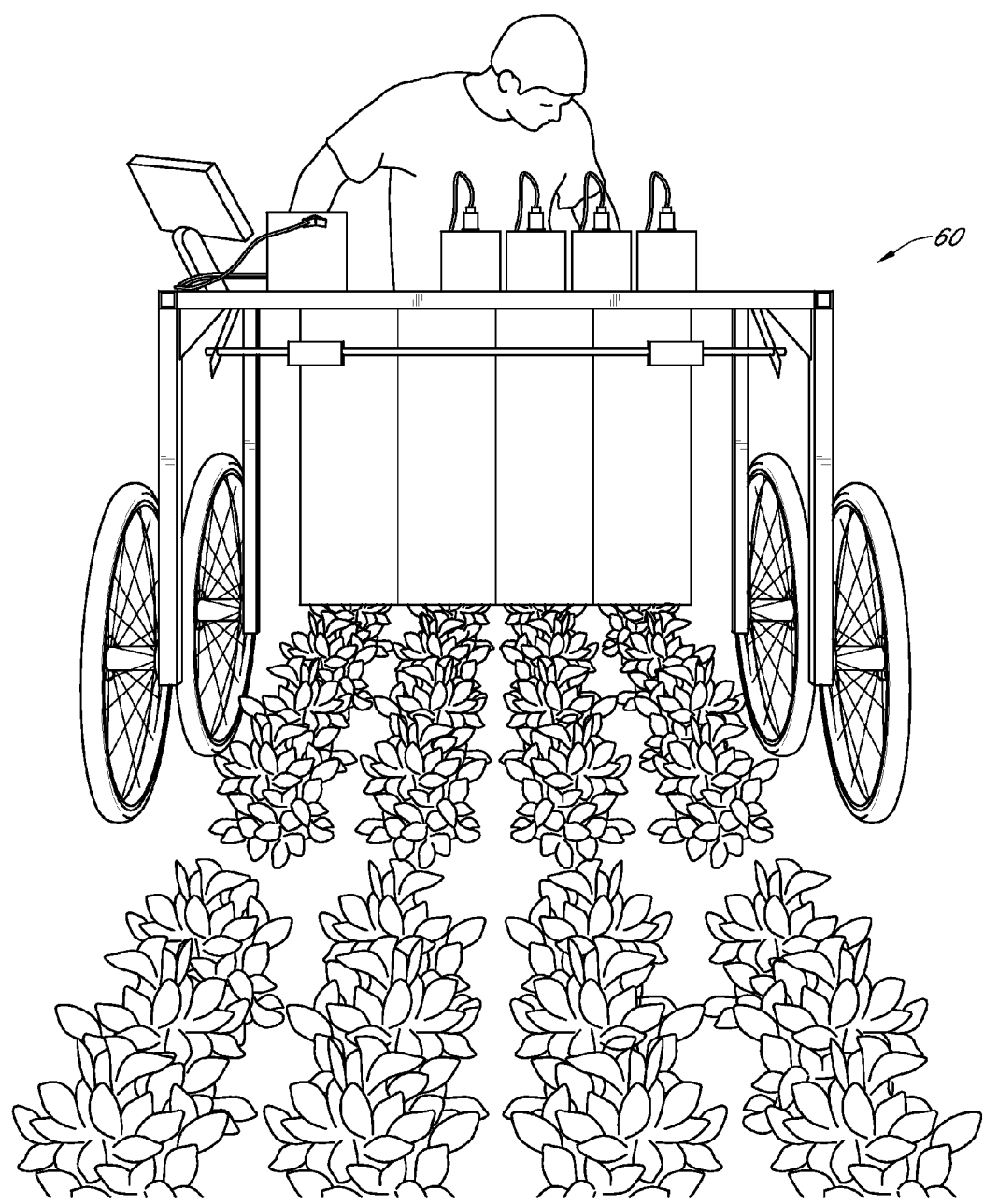
FIG. 12 is another perspective view of the field cart of FIG. 11.

As shown in FIG. 6, a field cart 60 includes a body 65, a sensor housing 70 mounted to the body 65, a computer 75, and a power supply 80. The body 65 includes a substantially rectangular frame 85 supporting a workspace 90. The body 65 also includes four legs 95, each of the legs 95 extending substantially perpendicularly from the frame 85. A wheel 100 is mounted to each leg 95 opposite from the frame 85. The four wheels 100 are grouped as two front wheels and two rear wheels and as two right-side wheels and two left-side wheels. FIGS. 11 and 12 provide additional views of the field cart 60.

Figure 7:
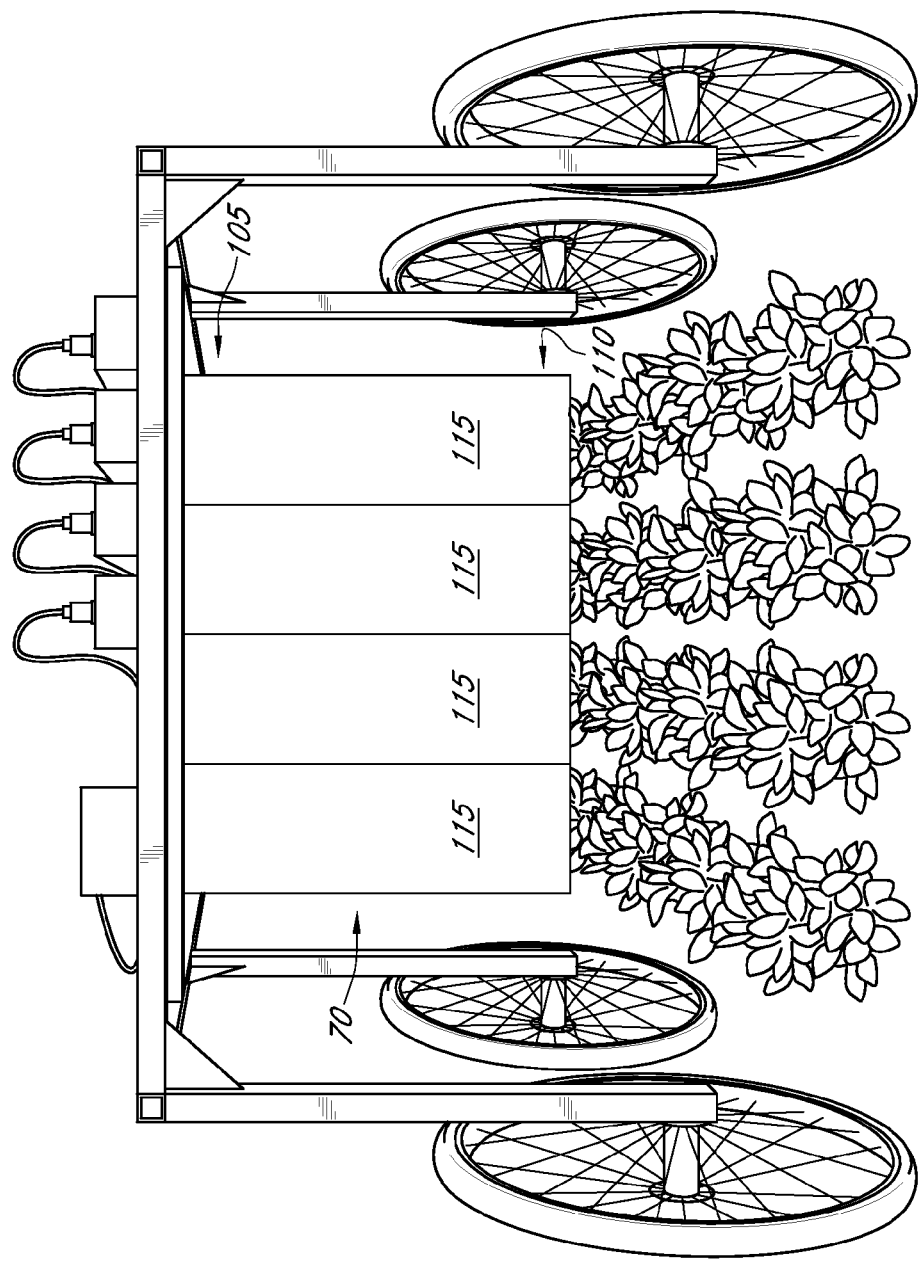
FIG. 7 is a front view of the field cart of FIG. 6.
Figure 8:
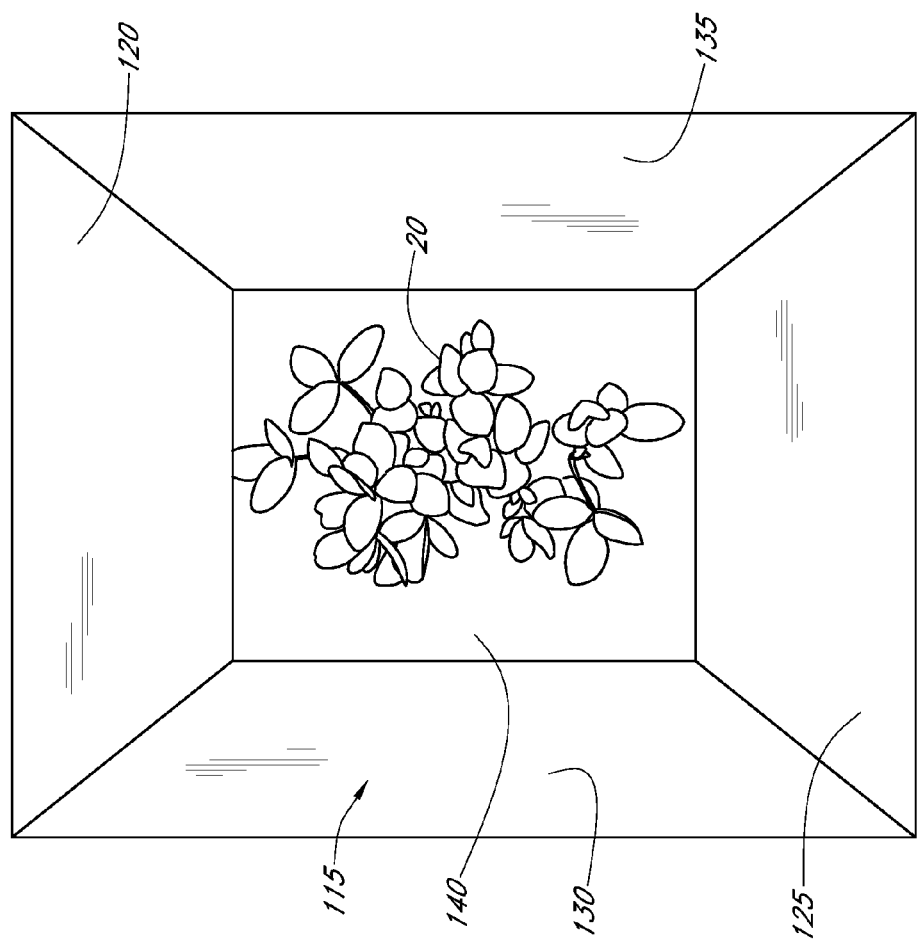
FIG. 8 is a top view of a partition of a sensor housing of the field cart of FIG. 6.

As shown in FIG. 7, the sensor housing 70 extends from a housing top 105 to a housing bottom 110 and is divided into four partitions or compartments 115. As shown in FIG. 8, each partition 115 has a first wall 120, a second wall 125, a third wall 130, and a fourth wall 135. The walls 120, 125, 130, and 135 are a neutral color, for example, grey. The generally planar first wall 120 is opposite from and generally parallel to the second wall 125. The generally planar third wall 130 is generally perpendicular to both the first wall 120 and the second wall 125. A fourth wall 135 is opposite from and generally parallel to the third wall 130. The first wall 120, the second wall 125, the third wall 130, and the fourth wall 135 define an interior volume with an opening 140. The spacing of the walls 120, 125, 130, and 135 of each partition 115 corresponds to the spacing of the micro-plots 20 in each range 35 so that when the sensor housing 70 is positioned above a range 35, each partition 115 is positioned above a single micro-plot 20. The sensor housing 70 is adjustable in the vertical direction to allow the housing bottom 110 to be raised if necessary for clearance above the top of the micro-plots 20. In a preferred embodiment, the first wall 120 and the second wall 125 are spaced twelve inches apart, the third wall 130 and the fourth wall 135 are spaced ten inches apart, with the housing bottom 110 positioned twelve inches above the ground and the sensor housing 70 extending thirty inches from housing top 105 to housing bottom 110. In practice, the opening 140 acts to limit the view of the sensor 40 to a single micro-plot 20 of soybean plants.

Figure 9:
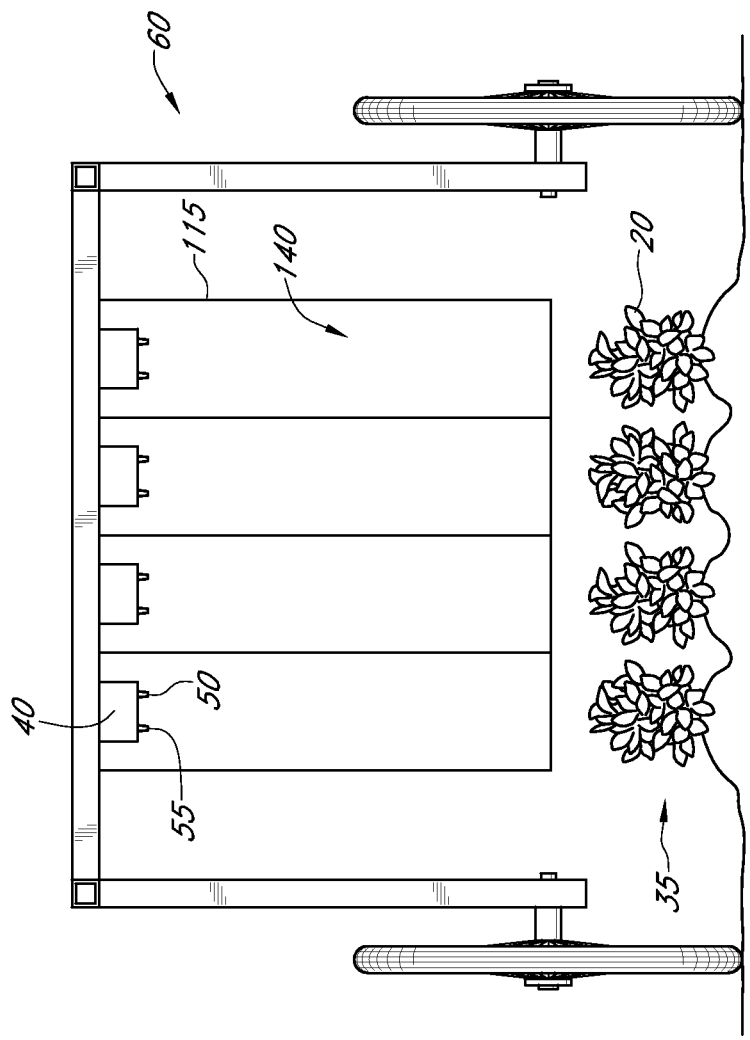
FIG. 9 is a cross-sectional view of the field cart of FIG. 6 showing the sensor housing partitions.

As shown in FIG. 9, a sensor assembly 40 is positioned within the interior volume 140 of each partition 115 with the light source 50 oriented longitudinally so that the light source 50 is generally parallel to the third wall 130 and the fourth wall 135 (FIG. 8). Each sensor assembly 40 is secured to the field cart 60. Each sensor assembly 40 is electrically connected to the computer 75 and is powered by the power supply 80 (FIG. 6). In a preferred embodiment, the light source 50 transmits a narrow band of red and infrared light modulated at 50 ms. with the sensor assembly 40 configured to take twenty readings per second. In a preferred embodiment, the bottom of the sensor assembly 40 is positioned about twenty-nine inches above the housing bottom 110.

Figure 10:
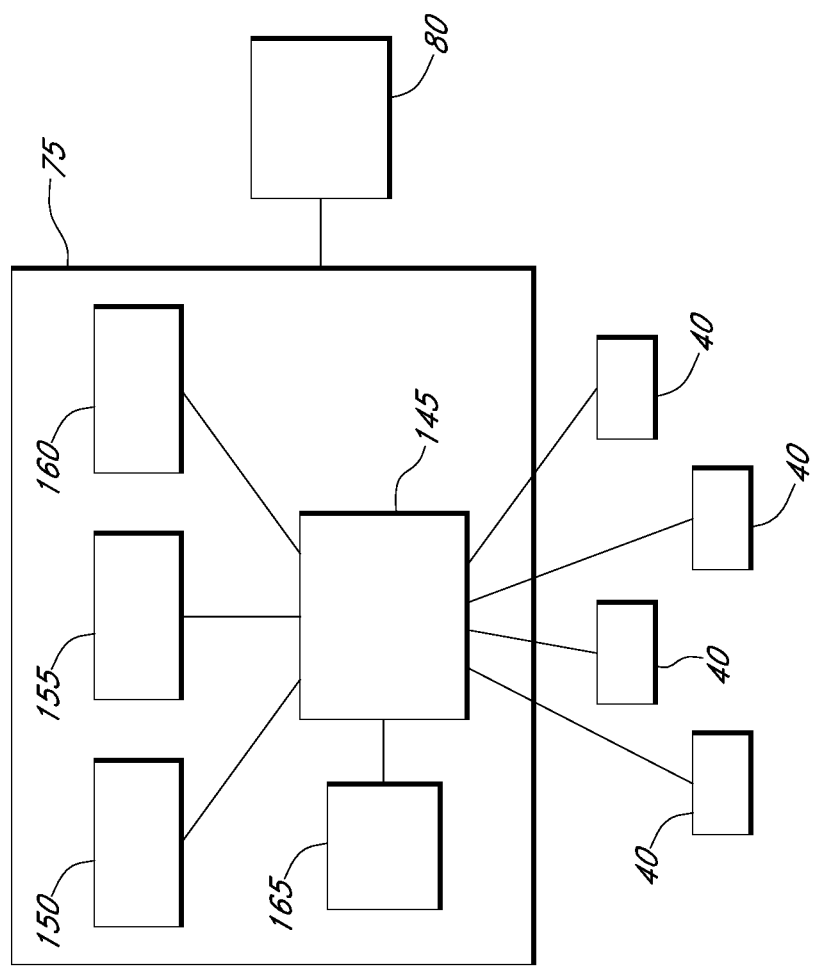
FIG. 10 is a schematic diagram of apparatus used in the field cart of FIG. 6.

As shown in FIG. 10, the computer 75 includes a processor 145, a memory unit 150 electrically connected to the processor 145, a user interface 155 electrically connected to the processor 145, a display 160 electrically connected to the processor 145, and a GPS system 165 electrically connected to processor 145. The GPS system 165 can be a stand-alone component or physically integrated with the computer 75. The sensors assemblies 40 are electrically connected to the processor 145. The computer 75 is electrically connected to the power supply 80. A computer software program is used to calibrate, control and record data of the phenotyping. The computer 75 is supported on the workspace 90. Alternatively, a GPS system 165 is not included in the computer 75.

The technician uses the field cart 60 to simultaneously scan all the micro-plots 20 in one range 35. During a scan, each sensor assembly 40 measures the reflectance and absorbance of one or more frequencies of light from a micro-plot 20 in NDVI units. NDVI values are on a continuous numeric scale between zero and one, where a high number indicates a micro-plot 20 with normal growth and a low number indicates a micro-plot 20 that is adversely affected by IDC impacted. The measured NDVI values are a composite of the values associated with all of the plants that make up a single micro-plot 20. The ability to make precise inferences is improved by using a continuous scale compared to the indexed numerical scale used with manual phenotyping. The sensor assemblies 40 are calibrated to a known standard and provide consistent readings across an experimental field 25, thus reducing or eliminating the subjective variation across multiple technicians and the range-to-range, day-to-day variation of each technician.

A field 25 is planted using multiple varieties of soybeans according to a planned experiment, preferably using a planter that was equipped with a GPS device such that the location of each micro-plot 20 is recorded together with the identity of the variety of seed planted in the corresponding micro-plot 20. The planned experiment lays out micro-plots 20 arranged in a grid of rows 21 and ranges 35 and organized as blocks 30. The planting location and identity data is loaded into the computer 75. The computer program is used, together with the GPS system 165 to record the data gathered by the sensor assemblies 40 and associate that data with the location and identity data.

As shown in FIG. 6, a technician pushes the field cart 60 along the rows 21 such that a range 35 of micro-plots 20 passes between the left-side wheels 100 and the right-side wheels 100. The technician positions the field cart 60 so that the sensor housing 70 is positioned above the first range 35 of the block 30. As shown in FIG. 8, the partitions 115 isolate the field of view for each sensor assembly 40 to a single micro-plot 20. The technician then triggers the sensor assemblies 40 to scan. The scan is triggered with the computer program by the user interface 155. After the scan is completed, the technician pushes the field cart 60 ahead to the next range 35. Alternatively, this field cart can be mobilized by addition of a motor, or it can be pulled behind a vehicle such as a truck, tractor, all wheel terrain vehicle, a mower, etc. This scanning sequence is repeated until all the ranges 35 in the block 30 have been scanned and until the desired number of blocks 30 has been scanned. Approximately two thousand micro-plots 20 can be screened in an hour using this automated method, more can be done with the mechanization of the movement of cart associated with the sensors. Compared to manual phenotyping methods the automated system is more objective and data collection at least two times faster. Alternatively, the scan can be triggered using a switch, a button, or other known methods of generating an electrical signal.

When using a computer 75 without a GPS system 165, the technician manually verifies the location of field cart 60 at the start of a group of rows 21. When the field 25 is planted, a stake is placed in the ground at the start of a group of rows 21. Another stake is placed in the ground after every twenty ranges 35. Each stake includes an individual identifier, for example a number or barcode. As the technician pushes the field cart 60 along the group of rows 21, the technician uses the stakes to verify the actual position of the field cart 60 compared to the expected location of the cart as determined by the computer program. For example, at the beginning of a group of rows 21, the computer program prompts the technician to verify the position of the field cart 60 using the stake at the beginning of the group of rows 21. Next, the technician inputs the identifier associated the stake and positions the field cart 60 above the first range 35 of micro-plots 20. Then, the technician triggers a scan. The computer program stores the data from the scan of the first range 35 and associates that data with the planned experiment. Then, the computer program automatically indexes to the second range 35. Next, the technician positions the field cart 60 above the second range 35 and repeats the scanning process. These steps repeat until twenty ranges 35 (four blocks 30) have been scanned. Then, the computer program prompts the technician to verify the position of the field cart 60 using the stake placed after the twentieth range 35. In this manner, the position of the field cart 60 in the field 25 is tracked to ensure that the computer program is correctly associating the data collected by the sensor assemblies 40 with the preplanned experiment. The technician can use the computer program to monitor his position along the group of rows 21 relative to the stakes. If the field cart 60 is not in the expected position when the technician is prompted, the technician can use the computer 75 and computer program to correct the error or to identify the ranges 35 that were incorrectly associated with the planned experiment.

When using a computer 75 including a GPS system 165, the location of each range 35 of plants is automatically determined by the GPS system 165 and the data from the sensor assemblies 40 is automatically associated with planned experiment after a scan is performed. Alternatively, the GPS system 165 determines the location of each block 30 and the computer program automatically indexes to the next range 35 after a scan.

Example One

Experiment Design and Phenotyping

The twelve F4 populations were developed into 12-2 replication trials at each of three locations, to determine phenotyping data. The experiment design was RCB (Randomized Complete Block) with a repeating check every 10th plot. Material CL968413 was the repeated check. Six seeds per plot were planted in a hill style fashion. Rows were 10 inch spacing and the hills were centered 15 inches down the row. The three location names were in Truman, Minn.; Ogden, Iowa; and Fort Dodge Iowa.

At approximately the V2-V3 growth stage, the plots were visually rated and canopy reflectance or NDVI (Normalized Difference Vegetation Index) measured with a Greenseeker RT100 radiometer for Yellow Flash traits. The visual rating and scanning was repeated 14 days later for the recovery traits. Visual ratings scale was 1-9 with 1 being the best and nine being the worst. Arithmetic averages of the visual and radiometer traits were calculated. Table 1 is a descriptive table of the traits measured and calculated.

TABLE 1

| | Phenotyping Traits | | | | |
|---|---|---|---|---|---|
| Trait Code | Description | Type | Min Value | Max Value | Calculation |
| ICFLR | Iron Deficiency Chlorosis Yellow Flash Rating | Rating | 1 | 9 | |
| ICR_R | Iron Deficiency Chlorosis Recovery Rating | Rating | 1 | 9 | |
| IC_R | Iron Deficiency Chlorosis Rating Calculated from Flash & Recovery Mean | Calculation | 1 | 9 | (ICFLR + ICR_R)/2 |
| ICFLN | Iron Deficiency Chlorosis Yellow Flash Radiometry Number | NDVI | 0 | 1 | |
| ICR_N | Iron Deficiency Chlorosis Recovery Radiometry Number | NDVI | 0 | 1 | |
| IC_N | Iron Deficiency Chlorosis Radiometry Number Calculated from Max Flash and Recovery Mean | Calculation | 0 | 1 | (ICFLN + ICR_N)/2 |

Thus, the invention provides, among other things, a system and apparatus for automated phenotyping of soybean plants to screen for iron deficiency chlorosis. Various features and advantages of the invention are set forth in the following claims.

What is claimed is:

1. A system for phenotyping soybean plants for evidence of iron deficiency chlorosis, the system comprising:
    (a) a row of soybean plants comprising a plurality of micro-plots of one or more soybean plants;
    (b) iron deficiency chlorosis sensing apparatus;
    (c) the sensing apparatus mounted on the vehicle for transport of the sensing apparatus over the row of soybean plants, wherein said sensing apparatus is positioned proximate the soybean plants;
    (d) a sensor housing restricting the field of the sensing apparatus to a single micro-plot;
    (e) a data signal generated by the sensing apparatus corresponding to the evidence of iron deficiency chlorosis of the plant or plants in the single micro-plot; and
    (f) a computer for receiving and storing the data signal associated with each micro-plot.

2. A system of claim 1, wherein said micro-plots are arranged in a plurality of rows separated by a preselected distance and wherein said sensor housing is divided into a corresponding plurality of partitions each of which is provided with a sensing apparatus, wherein the sensing apparatus are separated by the preselected distance and each has its field restricted to a single row by the corresponding partition.

3. A system of claim 1, further comprising location information for each micro-plot accessible by the computer and location determining apparatus on the vehicle to generate location information of the sensing apparatus to correlate the data signal to the corresponding micro-plot.

4. A system of claim 3, wherein the location determining apparatus includes a global positioning satellite (GPS) system.

5. A method for measuring susceptibility of a variety of soybean to iron deficiency chlorosis, comprising the steps of:
    (a) planting seed of a selected variety of the soybean in a micro-plot and recording the position of the micro-plot;
    (b) growing the plants to a selected stage for evaluation of susceptibility to iron deficiency chlorosis;
    (c) collecting radiometric sensor data from each micro-plot corresponding to the effect of iron deficiency chlorosis of a plant or plants in the micro-plot; and
    (d) analyzing the sensor data to generate a measure of the susceptibility of the variety of soybean to iron deficiency chlorosis in the micro-plot.

6. The method of claim 5, wherein GPS is used to record the location of seed planted in the micro-plots.

7. The method of claim 6, wherein GPS is used to correlate the sensor data to the location of the micro-plots.

8. The method of claim 5, wherein varieties of soybean plants of known susceptibility to iron deficiency chlorosis are included as check plants.

9. The method of claim 5, wherein the sensor is mounted on a vehicle and supported above the plants.

10. A method of plant breeding, comprising the steps of:
    (a) planting seed of a selected variety of the soybean in a micro-plot and recording the position of the micro-plot;
    (b) growing the plants to a selected stage for evaluation of susceptibility to iron deficiency chlorosis;
    (c) collecting radiometric sensor data from each micro-plot corresponding to the effect of iron deficiency chlorosis of a plant or plants in the micro-plot;
    (d) analyzing the sensor data to generate a measure of the susceptibility of the variety of soybean to iron deficiency chlorosis in the micro-plot; and
    (e) using the measure of susceptibility of the variety of soybean to iron deficiency chlorosis as a basis for selecting between soybean plants in a plant breeding program.

* * * * *